United States Patent [19]

Sireul et al.

[11] Patent Number: 4,944,501

[45] Date of Patent: Jul. 31, 1990

[54] EXAMINATION BED FOR NMR OR TOMODENSITOMETRY APPARATUS

[75] Inventors: Jacques Sireul, Wissous; René Gauthier, Antony, both of France

[73] Assignee: General Electric CGR SA, Issy les Moulineaux, France

[21] Appl. No.: 313,976

[22] PCT Filed: Jul. 10, 1987

[86] PCT No.: PCT/FR87/00278

§ 371 Date: Mar. 9, 1989

§ 102(e) Date: Mar. 9, 1989

[87] PCT Pub. No.: WO88/00451

PCT Pub. Date: Jan. 28, 1988

[30] Foreign Application Priority Data

Jul. 18, 1986 [FR] France ............................. 86 10475

[51] Int. Cl.⁵ .............................................. A61G 13/00
[52] U.S. Cl. ................................................... 269/322
[58] Field of Search ................... 269/322, 323, 71, 73, 269/242, 60, 61, 58; 108/137, 143; 384/418, 419; 378/209, 208, 177; 14/69.5, 71.1; 254/95

[56] References Cited

U.S. PATENT DOCUMENTS

| | | |
|---|---|---|
| 1,213,800 | 1/1917 | Piper ........................................ 254/97 |
| 2,765,201 | 10/1956 | Phillips ..................................... 254/95 |
| 3,588,500 | 6/1971 | Koerner ................................... 269/323 |
| 3,845,946 | 11/1974 | Warden et al. ......................... 269/323 |
| 3,944,204 | 3/1976 | Cesar ....................................... 269/323 |
| 4,131,802 | 12/1978 | Braden . |
| 4,545,571 | 10/1985 | Chambron ............................. 269/322 |
| 4,821,393 | 4/1989 | Spigarelli .............................. 269/242 |

FOREIGN PATENT DOCUMENTS

| | | |
|---|---|---|
| 0135161 | 3/1985 | European Pat. Off. . |
| 0197827 | 10/1986 | European Pat. Off. . |
| 0200374 | 12/1986 | European Pat. Off. . |
| 1273267 | 8/1961 | France . |
| 1436619 | 3/1966 | France . |
| 2151992 | 7/1985 | United Kingdom . |

Primary Examiner—Robert C. Watson
Attorney, Agent, or Firm—Oblon, Spivak, McClelland, Maier & Neustadt

[57] ABSTRACT

An examination bed, notably for RMN or tomodensitometry, which includes a chassis, an examination plateau, and a mechanism for driving movement of the plateau with respect to the chassis and with respect to the apparatus wherein the moving mechanism includes a moving assembly with respect to the plateau and the chassis, elongated in its shape with one end being movable with respect to the chassis and whose other end is movable with respect to the plateau.

10 Claims, 3 Drawing Sheets

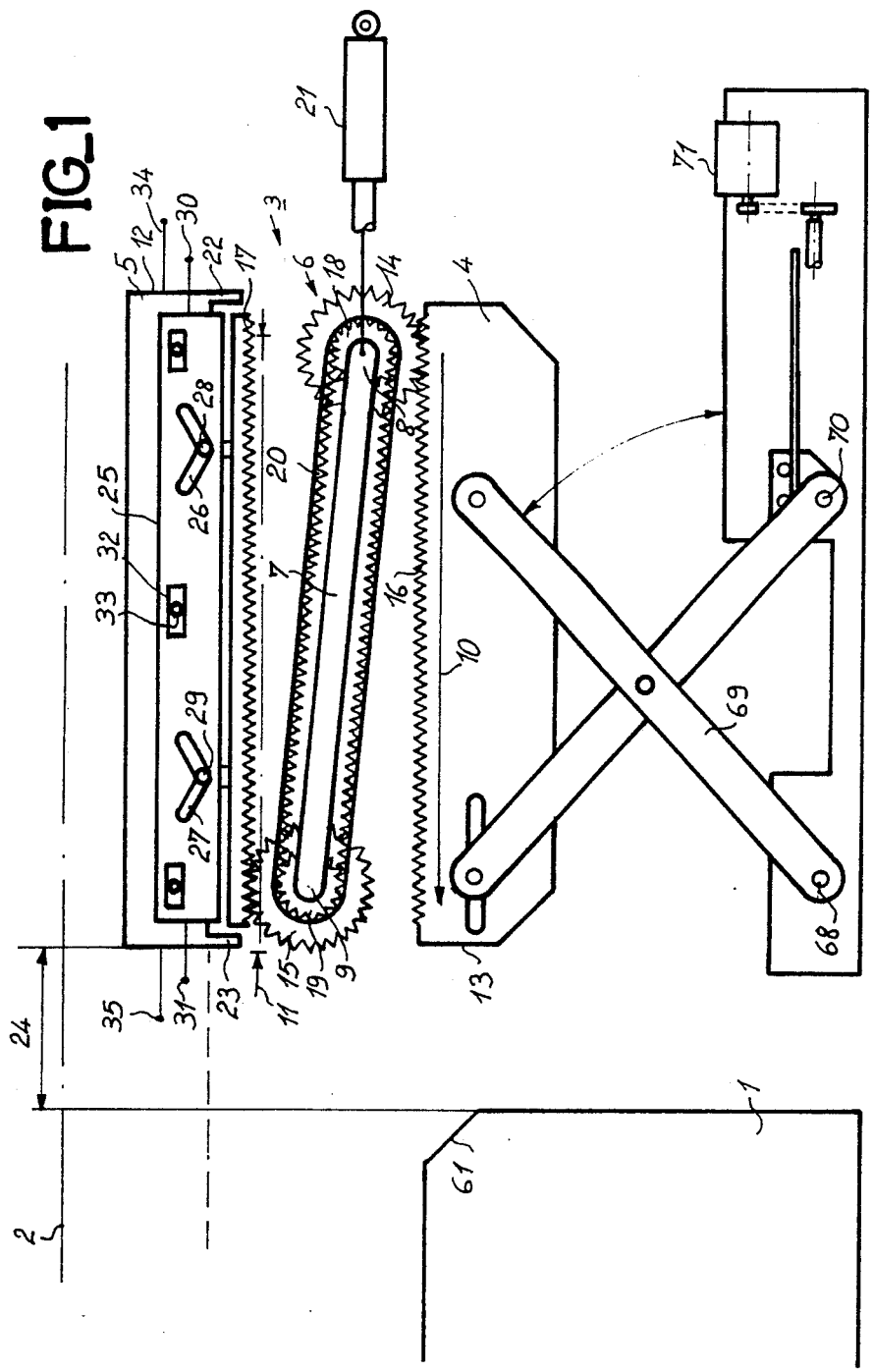

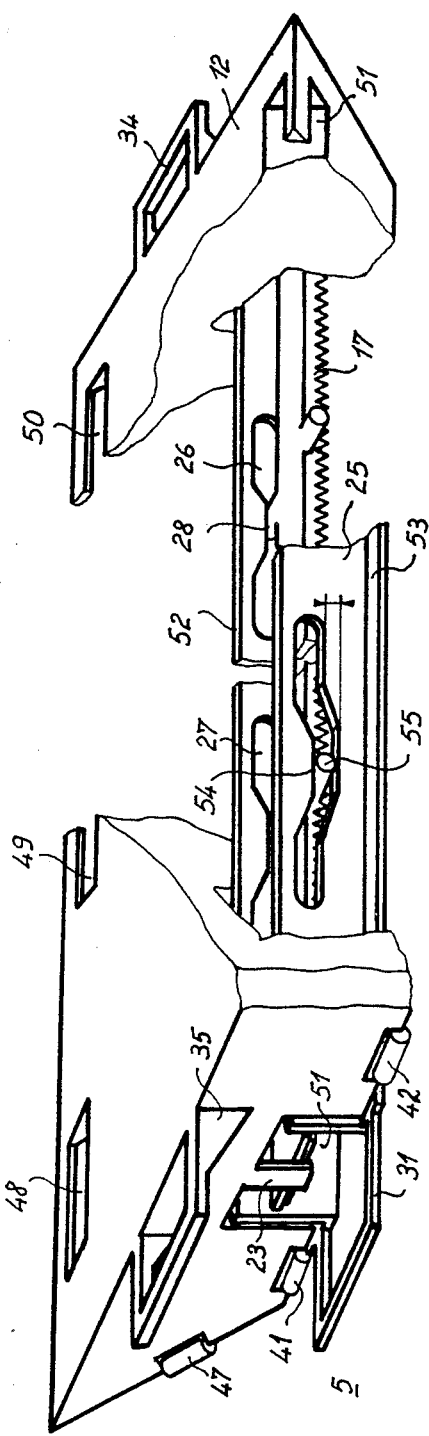
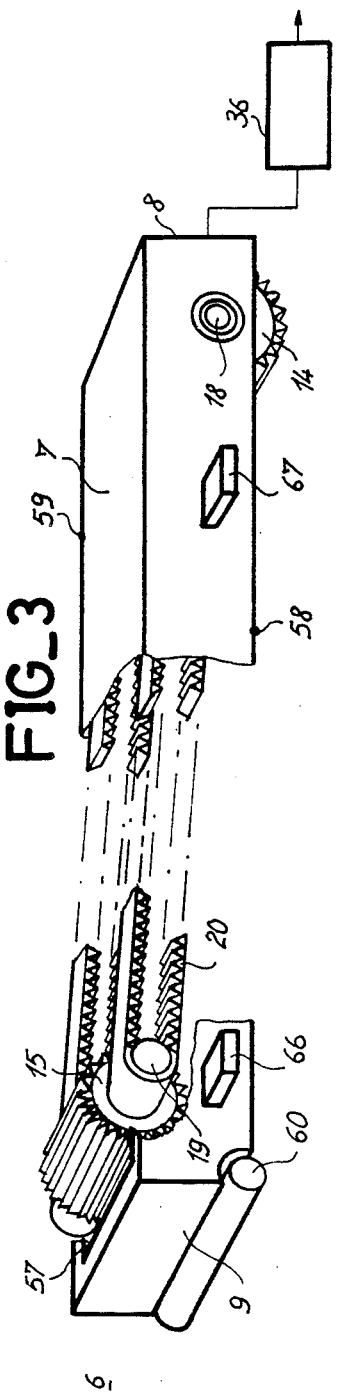
FIG_2
FIG_3

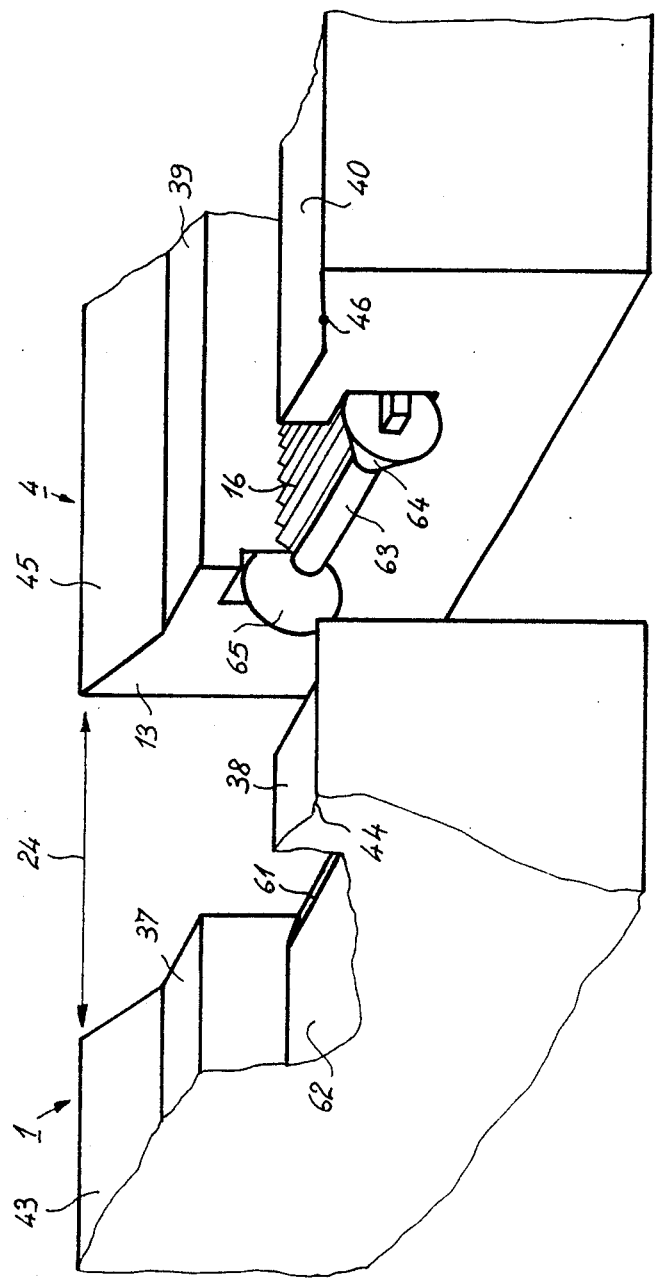

EXAMINATION BED FOR NMR OR TOMODENSITOMETRY APPARATUS

BACKGROUND OF THE INVENTION

1. Field of the invention

The present invention relates to a medical examination bed notably for a nuclear magnetic resonance (RMN) apparatus or a tomodensitometry apparatus. It is mainly used in the medical field where it is known that patients are made to lie down for non-invasive examinations with such machines.

2. Discussion of the Background

This type of examination is particular in that, in general, it takes a long time to perform. To improve the comfort of the patient, it may then be necessary to ventilate the machine examination tunnel and to illuminate and conduct dialogue with the patient. In all cases, it is also necessary to provide constant supervision of the latter. Indeed, patients going through such examinations are generally not in good health and because of this, may be upset by the examination resulting in them not feeling well. Under these conditions, they must be removed from the machine as quickly as possible. Under normal use, the insertion of the patient in the machine, on a plateau or a patient-support panel, is initiated by the starting of motors. These motors may be electrical. In the case of RMN, it is desirable to have them installed as far as possible from the examination tunnel so as not to interfere with the consistency of the magnetic field, through metallic mass. But the indisposition of the patient may be caused by a cut-off of power. The patient will be aware of the cut-off of lighting, ventilation and of supervision means and will feel some anguish. Intervention or extract of the patient from the machine is then rendered difficult because the plateau manipulation motors will have failed because of the lack of current. But because of the mechanical ratios and the demultiplication of these motors, it is unthinkable to attempt to turn the transmission chain backward by hand.

In addition, examination beds may be used for entering patients into the machine and in some cases bringing them into their bedrooms when examination is over. Therefore, the beds can be disconnected from the machines. This requirement of bed mobility is incompatible with the nature of the examination being undertaken. Indeed, for such examinations, images, sectional views of parts of the patient's body are taken. These images and sectional views correspond to particular parts of the patient's body. Therefore, it is necessary to identify and move precisely the part of the body to be imaged level with the imagery means. Consequently, when the bed is plugged into the machine, it is essential to bring the means for movement of the patient support panel on the bed to correspond exactly with the means for movement of the panel in the machine. To avoid this difficulty, long panels have been imagined, i.e. 3,50 meters long, still having one end engaged in the bed while the other is entered freely into the apparatus. It can be demonstrated that although already long, this panel may be insufficiently long to permit examination of the whole body. In this case the direction of patient presentation has to be inverted when the need arises. In addition, a long bed is difficult to manipulate through hospital corridors.

SUMMARY OF THE INVENTION

The present invention is designed to remedy the aforementioned drawbacks by proposing beds the plateau and means for driving the plateau include means to facilitate the manipulation of the patient. On the one hand, the plateau is rendered mobile to permit emergency withdrawals. This feature cannot be provided without guidance of the plateau on its chassis and through the apparatus with offset setting particularities for the position of the plateau with respect to the apparatus, such particularities being associated with a means of disengaging the plateau from the drive means ensuring its movement. These disengaging means permit exact replacement after emergency action. In addition, the mobile character of the plateau makes it possible to reduce the cost of the equipment to be built it is simply necessary to build a bed chassis and several mobile plateaus placed in turn on the bed chassis in order to be inserted into the machine. This results in the fact that the preparation of patients to be put through examination no longer requires immobilizing the bed and even less so the examination apparatus. On the other hand, movement of plateau with respect to the chassis of the bed for its insertion into the apparatus is ensured by using an auxiliary "differential" arm having a length similar to the length of the panel and/or chassis (2 meters) with one end of such arm driving the panel while the other rests on the chassis. In the invention, this is a way of separating the panel function, supporting the patient proper, from the panel means of movement function (over a distance greater than the useful length of the latter). The result is that the examination bed according to the invention has a conventional length adapted to its transportation through hospital corridors.

The present invention relates to an examination bed, notably for RMN or tomodensitometry apparatus comprising a chassis, an examination plateau and means for moving the plateau with respect to the chassis and to an apparatus wherein the moving means comprise an assembly, elongated in its shape, that is mobile with respect to the plateau and chassis, one end thereof is movable with respect to the chassis and the other end is movable with respect to the plateau.

BRIEF DESCRIPTION OF THE DRAWINGS

The invention will be better understood from the reading of the description which follows and the examination of the accompanying figures. The figures are given for indicative reason and in no way limit the invention. In the figures, the same references denote the same elements. They show : FIG. 1 : a schematic view of an examination bed according to the invention; FIG. 2 : an exploded prespective view of the movable plateau of the examination bed according to the invention; FIG. 3 : a differential plateau manipulation arm; FIG. 4 : a perspective view of the guiding path of the plateau on its chassis and in the apparatus.

DESCRIPTION OF THE PREFERRED EMBODIMENT

FIG. 1 is a schematic sectional view of an examination bed according to the invention. An RMN apparatus or a tomodensitometer 1 is provided to receive, substantially in line with its axis of insertion 2, the patient's body (not shown) supported by an examination bed in accordance with the invention. This examination bed includes a chassis 4, a plateau 5 and drive means 6 for moving the plateau with respect to the chassis and the apparatus. The invention is characterized by the drive means 6 being a moving assembly of elongated shape. This moving assembly includes an arm 7, wherein one end 8 thereof can be moved with respect to the chassis and the other end 9 thereof can be moved with respect to the plateau. Independent of the retention and supporting forces which will be explained subsequently, it can be understood that each point of the plateau can be moved with respect to any point of the chassis by a length equal to the sum of the useful travel 10 of end 8 with respect to the chassis and of useful travel 11 end 9 with respect to the plateau. In addition, the arm causes the two end positions of the plateau to be offset with respect to the center of the chassis. In the representation of FIG. 1, the plateau is at an end position suitable for preparation for its insertion into the machine. In the other end position, plateau 5 is completely advanced into machine 1 and the rear end 12 of the plateau may be distant from the front end 13 of the chassis by a distance substantially equal to the length of arm 7.

In the example shown, the mobile assembly 6 includes two gear wheels 14 and 15 rotating on shafts integral with the respective ends 8 and 9 of the arm. Gear wheel 14 bears on a rack 16 integral with the chassis while gear 15 bears on a rack 17 connected to the plateau. Pinons, preferably including teeth 18 and 19, are respectively rendered integral with the gears 14 and 15. The pinons rotate about themselves about axes collinear with the wheel shafts. A continuous belt 20, preferably toothed, is tensioned and meshes about the pinons. By a motor means, schematically shown by a ram 21, it is possible to push end 8 of arm 7. Rack 16 then causes gear 14 to turn driving pinon 18 and through belt 20, driving pinon 19. Pinon 19 in turn drives the rack 17 of plateau 5 in its movement. The longitudinal movement of rack 17 is limited by two stops 22 and 23 integral with plateau 5.

Consequently, plateau 5 moves with respect to end 9 of the arm by a length related to the movement of end 8 with respect to the chassis 4. The transformation ratio of the movements can be adapted by adjusting the diameters of gears 14 or 15 and/or the diameters of pinons 18 and 19 integral with these gears. In a preferred embodiment, the transformation ratio is 1.

The embodiment could be achieved by other means. For instance, it would be possible to obtain a moving assembly 6 with a triple jack, i.e. with at least three interleaved rods. A first rod would have one end attached to the plateau and a third external rod would have one end, that is opposite the end of the first rod, attached to the chassis. Under these conditions, it is equivalent to consider the second rod as forming the mobile assembly and having a first end movable with respect to the plateau and a second end movable with respect to the chassis. This solution with hydraulic rams can be replaced by an equivalent screw solution with at least three screws interleaved in one another.

In addition to the end elements, the intermediate elements, the rams or the srews form the mobile assembly. When the intermediate elements are single, the mobile assembly is rigid and non-deformable. It corresponds to a rigid bar 7. If the intermediate elements are more numerous, for instance if they include at least interleaved rods, the length of the intermediate element can be variable. In all cases, the invention also offers the advantage of making it possible to approach chassis 4 of the equipment 1 while leaving between these two parts a space 24 which can be used for any patient preparation operation before the insertion of the patient in a machine. For instance it is possible for an operator to enter the space 24 to arrange the position of the patient's head on the plateau 5, in particular when the head is wearing part of the measurement means needed for the examination to be undertaken, in particular for RMN. Indeed, examination of the head must be carried out while making sure that the head cannot move during the examination. Therefore, it must be held to prevent it from moving in the image. This retention, which is unpleasant for the patient, must be undertaken at the latest possible stage in order not to frighten the patient. In practice, it is carried out just before entry into machine 1. Without the presence of mobile assembly 6, it would be necessary to insure the fullest possible useful travel of the plateau, to subsequently approach the plateau as close as possible to the machine entry front.

The plateau 5 is further provided means of rendering it movable upon an emergency occurring. Schematically, FIG. 1 depicts plateau 5 retaining a drive rack 17 which meshes with mobile assembly 6 to move the plateau. The rack, maintained in its longitudinal movement by two stops 22 and 23 integral with the plateau, can nevertheless sustain a vertical retraction, disengaging movement, tending to lift it. In this manner, the teeth of gear 15 of the mobile assembly escape the notches of rack 17. In one example, the disengaging movement is obtained by means of a plate—cam 25 which maintains in slots, generally V- shaped, such as 26 and 27, supporting shafts, respectively 28 and 29 of rack 17. By simplification, plate 25 is designed to move longitudinally by means of handles 30 or 31 located either side of the plate 5. It is horizontally movable by means which will be described subsequently and serve the same roll as the longitudinal windows such as 32 of plate 25, sliding along dowels 33 of plateau 5.

By operating either of the handles, plate 25 is made to move to right or to left and drives upward the shafts 28 and 29. Under these conditions, the rack rises and escapes the teeth of gear 15. By working in this manner, the means for moving plateau 5 are disengaged. It is then possible to slide the plateau on its supporting means. To facilitate the operation of handle 30 or 31, such handle is matched with another handle, respectively 34 or 35, integral with the plateau and has a longitudinal offset the value of which is approximately equal to the useful displacement length of plate 25 with respect to the plateau. In practice, taking account of the depth of the teeth in gear 15 and rack 17, and the inclination of the V of the slots 26 or 27 (approximately 30°), it is possible to grasp in one hand both handles 30 and 34 or 31 and 35. By closing the hand, disengaging of the rack 17 occurs. The force needed to attain this result is low because the rack weight is relatively, light. In one example, this effort has been evaluated as being a force of approximately 2 kg force. Then, by maintaining the two handles against one another, it is possible to displace plateau 5 in the desired direction in order to extract machine 1.

FIGS. 2 to 4 show a particular example of the construction of plateau 5, moving assembly 6 and chassis 4. As an additional and essential feature, the examination bed according to this invention includes measuring means 36 of the end position 8 of moving assembly 6 with respect to chassis 4. The means 36 may include a tachogenerator or resolvers mounted on gear shaft 18. Since the chassis is designed for being located in a predetermined space 24 of apparatus 1, and since the plateau is, in the normal transportation position of the bed, at a predetermined end position with respect to the chassis, by counting the number of turns effected by the gear 14 or the pinon 18, it is possible to know where any section of the plateau is located in the machine when it is advanced into it. This arrangement offers the advantage of permitting highly tolerant positioning of plateau 5 in the machine. Finally, the conditions of the alignment of plateau 5 with the machine are no longer critical, even for measuring penetration into the machine.

By this method, it is possible to construct a plateau having a V-shape section (FIG. 2), designed to slide on corresponding shaped guides in the apparatus and in the chassis (FIG. 4). The apparatus and the chassis, in a preferred manner, include supporting areas numbered 37-38 and 39-40 designed to receive bearing rollers such as 41-42 (FIG. 2) of plateau 5. In a preferred example, the rollers are of epoxy glass fiber coated with rubber. This provides flexibility for the support and avoids subjecting the patient to disagreable shaking. To ensure the guidance of the plateau in the machine and the chassis of the bed, these include inclined planes, respectively 43-44 and 45-46 which bear against rollers such as 47 of the plateau 5. In practice, the angle of inclination of the inclined plates is around 30°. This is a compromise between the guidance efficiency to be obtained and the limits at which the rubberized linings come off the glass rollers. In one example, to support the plate, approximately two dozen rollers such as rollers 41-42 are used. For the guide, approximately half a dozen are placed on either side. The plateau can also include side handles such as 48 to 51, regularly distributed either side of the panel. With these handles, the plateau can be grasped and placed on a gurney for wheeling through the hospital. In one preferred embodiment, the disengaging device on the rack is slightly different. Rack 17 is flushed-fitted into a groove 51 inside the plateau. It is inserted between the two stops including stop 23 which is visible, integral with the plateau. Either side of the rack 17, in groove 51, are entered on edge, the two plates 25 and 52 being designed to play the same part and ensure symmetry of the lifting force of the rack 17. Handle 31 is designed to move longitudinally the two plates 25 and 52 at the same time. With respect to FIG. 1, the plate guiding device with respect to the plateau 5 has been modified. The plates are each provided with a shoe on their lower edge, such as 53 to bear beneath plateau 5 and thus play the same part as dowels 33 in holes 32. In a preferred manner, cams 26 and 27 have, at the edges and at the center of the V, flats forming positions of rests for the lifting force and maintain rack 17. Accordingly, the low and high positions of the rack are mechanically stable. The central flat on the cams, i.e. flat 54, is designed to apply pressure from top to bottom to the supporting shafts, i.e. shaft 55 of the rack to prevent, since the weight of the rack is low, that it lifts alone under the drive effect of gear 15. In one example, rather than two sets 26-27 of slots-cams, plates 25 and 52 include approximately ten of them. In this manner, there is no need to excessively rigidify rack 17.

Mobile assembly includes arm 7 in which the gears 14 and 15 move at either end. Arm 7 is in the form of a box provided with two openings, for instance opening 57 to permit gears 14 or 15 protrude beyond the respectively lower surface 58 and upper surface 59 of box 7. The arm also has a front roller 60 to permit its bearing in machine 1 when engaged in it. For this purpose, the input edge of the machine has a chamfer 61 (FIG. 1 and 4) to receive the roller and permit the insertion of the arm into a groove 62, provided in the machine tunnel. In this way, during the greater part of its transfer, the arm rests partly on rack 16 through gear 14 and partly in groove 62 through roller 16. At the exit of chassis 4 there is connecting block 63 designed to bear under boxed section 7 while head 9 of arm 7 crosses space 24. Tapered ends 64 and 65 of connecting block 63 cater for alignment faults between the machine. It is intended to provide the side edges of arm 7 with blocks such as 66 or 67, preferably of polytetrafluoroethylene to bear on the vertical sides of the grooves in chassis 4 and of machine 1. The overall height of the arm is calculated so that the arm can be housed within grooves 51 and 61 or between racks 16 and 17, without applying any supporting force to the plateau.

The bed and/or chassis according to the invention can also be provided with the aforementioned attached devices.

In addition, and by preference, the bed is adjustable as to height in order to suit all different machines and to facilitate the loading of any nonbedridden patient enabling him or her to sit on the plateau near the ground. The elevation of the bed is caused by the rotation of the legs of an X. In a preferred embodiment, base 68 of one of the legs, i.e., leg 69 is held fixed with respect to machine 1 while the base of the other leg can slide toward base 68 under the effect of motor 71. Under these conditions, a space or deviation 24 between the bed and the machine varies as a function of the bed's height in order to facilitate, even more in the low position, passage of the operator during rising movement. The bed is put through rotational movement to reduce the gap separating it from the machine.

Obviously, numerous modifications and variations of the present invention are possible in light of the above teachings. It is therefore to be understood that within the scope of the appended claims, the invention may be practiced otherwise than as specifically described therein.

We claim:

1. An examination bed, notably for a NMR or tomodensitometry apparatus, which comprises:
   a chassis;
   an examination plateau;
   moving assembly means for moving the plateau with respect to the chassis and said apparatus; and
   means for translating said moving assembly means with respect to said plateau, said chassis and said apparatus, said moving assembly means being elongated in shape, a first end of said moving assembly means including means for mechanically connecting said moving assembly means to said chassis and including means for moving said first end in translation with respect to said chassis and a second end of said moving assembly means including means for providing mechanical motion connection of said moving assembly means to the plateau, and means for moving said second end in translation with respect to said plateau wherein said means for translating said moving assembly means is connected to said moving assembly means.

2. A bed according to claim 1, wherein said moving assembly means includes an arm having a predetermined and fixed length and having, at said first and second ends of said moving assembly means, mobile drive means for moving said arm, respectively, in translation with respect to said chassis and said plateau with respect to said arm.

3. A bed according to claim 1 or 2, wherein said moving assembly means includes coupling means so that movements with respect to said first and second ends are mechanically dependent.

4. A bed according to claim 3, wherein said arm includes first and second drive gears which mesh with first and second racks respectively connected to said chassis and to said plateau.

5. A bed according to claim 4, wherein said means for moving said plateau with respect to said chassis includes a belt having teeth for meshing with said drive gears.

6. A bed according to claim 3, wherein said coupling means are such that the ratio of movement of said plateau with respect to said moving assembly means is one to one and the ratio of movement of said moving assembly means with respect to said chassis is one to one.

7. A bed according to claims 1 or 2, wherein said chassis includes, at an end near said apparatus, a coil provided with two cones opposed by an apex.

8. A bed according to claim 2, wherein said arm includes a roller positioned in an area adjacent said apparatus so as to form a support point of said arm upon positioning of said arm in said apparatus.

9. A bed according to claim 3, wherein said apparatus and said chassis include grooves for receiving said arm and wherein said arm includes side blocks for guiding said arm between sides of said grooves.

10. A bed according to claims 1 or 2, wherein said moving assembly means includes means for measuring the position of said plateau with respect to said apparatus and while simultaneously measuring the position of an end of said moving assembly means connected to said chassis.

* * * * *